United States Patent

Burton et al.

[11] Patent Number: 5,520,363
[45] Date of Patent: May 28, 1996

[54] OPHTHALMIC EXAMINATION CHAIR POSITIONING SYSTEM

[75] Inventors: Roy H. Burton, Columbus; David E. Wood, Grove City; Kevin W. Intrieri, Dublin, all of Ohio

[73] Assignee: R. H. Burton Company, Grove City, Ohio

[21] Appl. No.: 287,155

[22] Filed: Aug. 8, 1994

[51] Int. Cl.⁶ .................................................. F16M 13/00
[52] U.S. Cl. ..................................... 248/430; 297/344.14
[58] Field of Search ........................... 248/429, 424, 248/430; 297/344.14, 344.13, 344.11, DIG. 4

[56] References Cited

U.S. PATENT DOCUMENTS

| | | | |
|---|---|---|---|
| 2,553,652 | 5/1951 | Gradle | 248/430 |
| 3,259,355 | 7/1966 | Slouka | 248/430 |
| 3,741,513 | 6/1973 | Wilson | 248/429 |
| 4,027,747 | 6/1977 | Moorman, Jr. | 188/28 |
| 4,140,342 | 2/1979 | Jones | 297/261 |
| 4,278,387 | 7/1981 | Seguela et al. | 414/462 |
| 4,389,056 | 6/1983 | Tenniswood | 280/289 |
| 4,741,506 | 5/1988 | Schwaegerle | 248/430 |
| 4,768,831 | 9/1988 | Liedberg | 297/344.14 X |
| 4,911,435 | 3/1990 | Johns | 272/134 |
| 4,941,799 | 7/1990 | Gordon et al. | 414/678 |
| 5,007,118 | 4/1991 | Ebersole | 4/515 |
| 5,029,941 | 7/1991 | Twisselmann | 297/344.13 X |
| 5,040,939 | 8/1991 | Booth | 414/678 |
| 5,195,712 | 3/1993 | Goodall | 248/429 X |
| 5,220,116 | 6/1993 | Sheets | 42/94 |

*Primary Examiner*—J. Franklin Foss
*Attorney, Agent, or Firm*—Mueller and Smith

[57] ABSTRACT

A positioning system for moving an ophthalmic examination chair used in conjunction with an associated instrument stand between a forward position spaced a predetermined distance from an eye examination target and a rearward position providing access to the instrument stand by a patient in a wheel chair. A lower base is provided as extending along a longitudinal axis between a forward end and a rearward end, and as having an upper and a lower surface and a widthwise extent configured as being receivable between the wheels of the wheel chair. An upper carriage, having a bottom surface and a top surface configured to receive the examination chair thereon, is supported on the upper surface of the base for movement between the forward and the rearward end thereof along the longitudinal axis to position the examination chair at the forward and the rearward position. A locking assembly is employed to releasably lock the carriage in a forward orientation disposing the examination chair at the forward position, and in a rearward orientation disposing the examination chair at the rearward position.

28 Claims, 4 Drawing Sheets

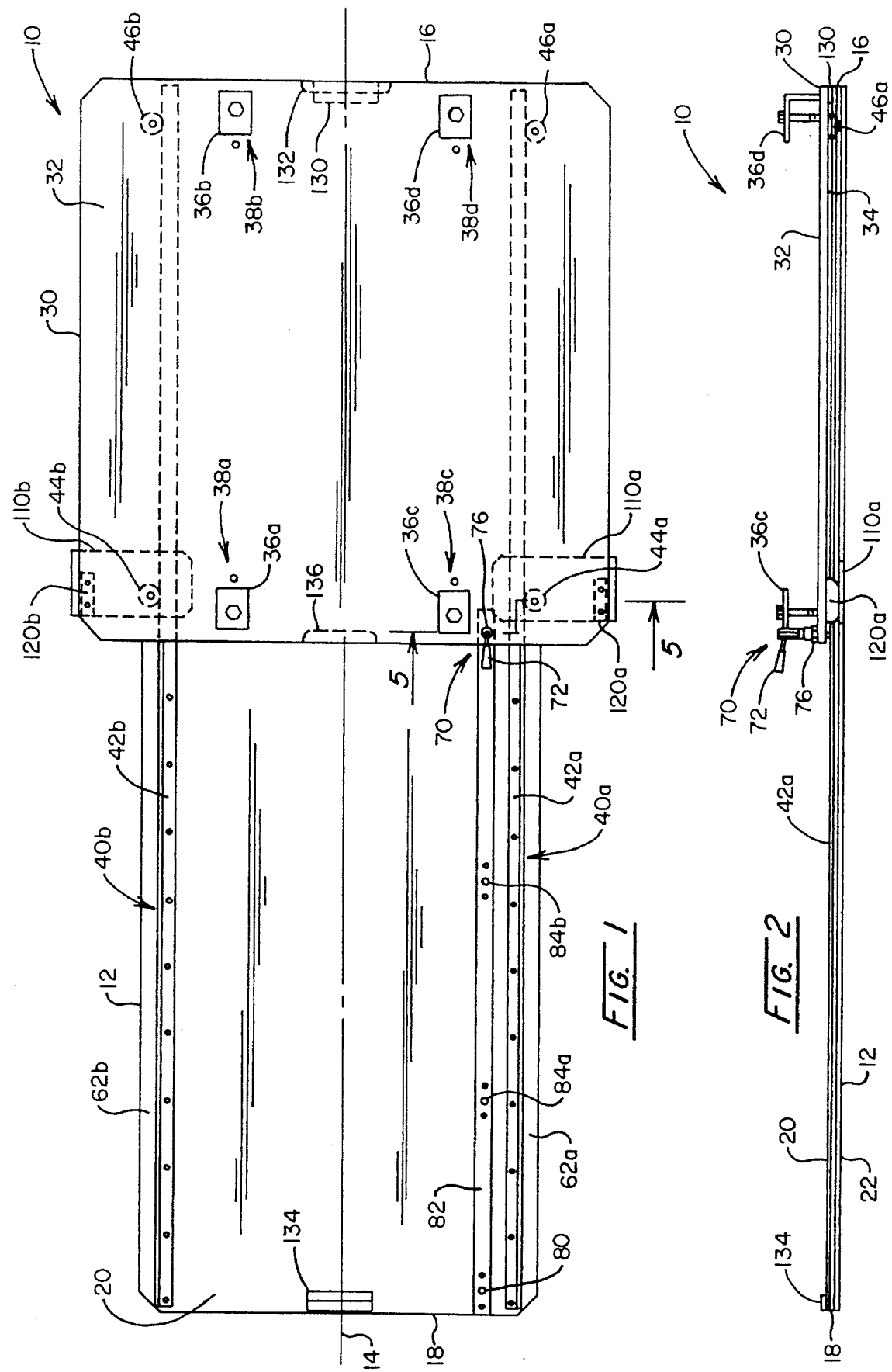

OPHTHALMIC EXAMINATION CHAIR POSITIONING SYSTEM

BACKGROUND OF THE INVENTION

The present invention relates generally to a positioning system for an ophthalmic examination chair which provides wheel chair access to the instrument stand to thereby accommodate the examination of disabled patients.

Nineteen ninety two heralded the passage of the Americans with Disabilities Act (ADA) which extended the protection of the federal civil rights laws to disabled Americans in such areas as employment, public accommodations, state and local government services, public and private transportation, and telecommunication services. In particular, Title II of the ADA, which applies to all private entities that own, operate, or lease a "place of public accommodation," prohibits such entities from discriminating against the disabled. Specifically, the ADA requires each and every "place of public accommodation" to insure that no individual with a disability is excluded, denied services, segregated, or generally treated differently from other individuals because of the absence of auxiliary aids and services adapted to accommodate the disability. Penalties for violations of the ADA include monetary fines as high as fifty thousand dollars for the first infraction and one hundred thousand dollars for subsequent infractions, as well as temporary or permanent injunctive orders requiring the altering of facilities to prohibit continuing discrimination. A tax credit, however, has been made available for "eligible access expenditures" to help mitigate the expense of modifying or acquiring equipment or devices for providing goods and services to the disabled.

Although the passage of the ADA generally has been praised as rightly affording the over 40 million disabled Americans equal access to all public places, compliance with the provisions of the act often has proven to be both costly and difficult for many industries, businesses, and services. The medical professions too have been confronted with the problem of how to comply with the requirements of the ADA. Indeed, ensuring that the disabled have unrestricted access to needed medical care may be seen as a motivating factor behind the passage of the ADA.

As with all health care providers, the providers of ophthalmic and optometric services, such as ophthalmologists, optometrists, opticians, and the like have been exploring various ways of meeting their obligation of reasonable accommodation under the ADA. As usually equipped, the standard ophthalmic examination room involves an instrument stand having a movable arm supporting a refractor assembly, which assembly contains a number of adjustable testing lenses and, optionally, other eye examination instruments such as a keratometer and a slit lamp. The stand additionally may support a holder for such hand-held diagnostic instruments as an ophthalmoscope and a retinoscope. An examination chair is associated with the stand and is positioned with respect thereto such that refractor assembly may be placed confronting the eyes of the patient being examined. With the patient and the refractor assembly properly positioned, the examination procedure commences with the darkening of the examination room, and the observing by the patient of a distant target, such as an eye chart or the like, through the lenses of the refractor assembly. The examination chair is positioned to space the patient a predetermined distance from the eye chart which is calibrated to be read from a specified distance by the patient. The lenses of the refractor assembly then are adjusted using a trial-and-error procedure until the desired degree of vision correction is obtained. As the trial-and-error procedure may become somewhat involved and protracted, the comfort of both the patient and the examiner is of great importance. Accordingly, most examination chairs are designed to be adjustable as to height or degree of incline via an internally-contained pneumatic, mechanical, or electrical arrangement. Such an arrangement, however, adds to weight of the chair which may weigh several hundred pounds unloaded.

Given the weight of the examination chair and the need for it to be positioned in close adjacency to the instrument stand and at a predetermined distance from the eye chart, it generally is considered to be neither movable or portable once placed within the examination room. Accordingly, the only options heretofore available for providers seeking to comply with the ADA requirements have been either to physically transfer the patient from the wheel chair to the examination chair, or to establish a separate examining room for wheel-chair-bound patients. A significant risk of personal injury, however, both to the patient and to the person or persons assisting the patient, attends the physical transferring of the patient out of the wheel chair and into the examination chair. With such risks of injury comes an increased liability to the provider. Moreover, many providers have neither the office space nor the funds necessary to establish a separate examining room and to equip it with specialized chairs and instrument stands specifically designed to accommodate the disabled. Accordingly, it will be appreciated that other, less-expensive alternatives for providers of eye care to conform to the provisions of the ADA would be welcomed by all of those involved.

BROAD STATEMENT OF THE INVENTION

The present invention is directed to a positioning system for an ophthalmic examination chair which provides wheel chair access to the instrument stand for accommodating the examining of disabled patients. In providing for the mounting of the examination chair on a platform formed as having a base and a carriage supported for movement along the base, the present invention allows for the facile repositioning of the chair from a forward position spaced a predetermined distance from an eye examination target to a rearward position providing access to the instrument stand by the patient in the wheel chair.

One aspect of the invention therefore involves a positioning system for moving an ophthalmic examination chair used in conjunction with an associated instrument stand from a forward position spaced a predetermined distance from an eye examination target. A lower base is provided as extending along a longitudinal axis between a forward end and a rearward end, and as having an upper and a lower surface and a widthwise extent configured as being receivable between the wheels of the wheel chair. An upper carriage, having a bottom surface and a top surface configured to receive the examination chair thereon, is supported on the upper surface of the base for movement between the forward and the rearward end thereof along the longitudinal axis to position the examination chair at the forward position and at a rearward position for providing access to the instrument stand by a patient in a wheel chair. A locking assembly is employed to releasably lock the carriage in a forward orientation disposing the examination chair at the forward position, and in a rearward orientation disposing the examination chair at the rearward position.

A further aspect of the present invention involves a method of providing access by patient in a wheel chair to an ophthalmic instrument stand having an associated examination chair disposed at a forward position spaced a predetermined distance from an eye examination target. The examination chair is mounted on a platform provided as having a lower base extending along a longitudinal axis between a forward end and a rearward end, and an upper carriage having a bottom surface and a top surface configured to receive the examination chair thereon. The base is formed as having an upper and a lower surface and a widthwise extent configured as being receivable between the wheels of the wheel chair. The carriage is supported on the upper surface of the base for movement between the forward and the rearward end thereof along the longitudinal axis to position the examination chair at the forward position and at a rearward position providing access to the instrument stand by the patient in the wheel chair. With the chair mounted on the platform, the carriage of the platform is moved rearwardly along the longitudinal axis of the base to move the examination chair from the forward position to the rearward position. The wheel chair then is moved rearwardly over the base of the platform, with the widthwise extent thereof being received between the wheels of the wheel chair. Lastly, the wheel chair is positioned at the forward position to space the patient at the predetermined distance from the eye target.

Advantages of the present invention include a positioning system for an ophthalmic examination chair providing efficient wheel chair access to the instrument stand in a minimum amount of space which is generally available in any examination room without the reconfiguration thereof. In allowing the disabled patient to remain seated in his or her wheel chair, the system also assures the dignity of the patient while eliminating the risk of personal injury which attends the removal of the patient from the wheel chair. Additional advantages of the present invention include the provision of a stable examination chair platform having a low profile which minimizes the hazard to ambulatory patients stepping down from the examination chair while under debilitating medications such as anesthetics or eye dilation drops. Further advantages include a platform having a carriage which may be moved with little effort, but which is lockable and self-positioning to return the examination chair to a calibrated forward position spaced a predetermined distance from an eye examination target. The platform additionally may be designed to automatically position the wheel chair at the same calibrated forward position. Still further advantages include a platform which is retrofittable to existing chairs and which thereby allows providers to inexpensively conform to ADA requirements. These and other advantages will become readily apparent to those skilled in the art based upon the disclosure contained herein.

BRIEF DESCRIPTION OF THE DRAWINGS

For a fuller understanding of the nature and objects of the invention, reference should be had to the following detailed description taken in connection with the accompanying drawings wherein:

FIG. 1 is a top view of a positioning system in accordance with the present invention for positioning an ophthalmic examination chair having an associated instrument stand between a forward position spaced a predetermined distance from an eye examination target and a rearward position providing access to the instrument stand by a patient in a wheel chair;

FIG. 2 is a side view of the positioning system of FIG. 1 shown in a forward orientation for disposing the examination chair at its forward position;

Figure 3:
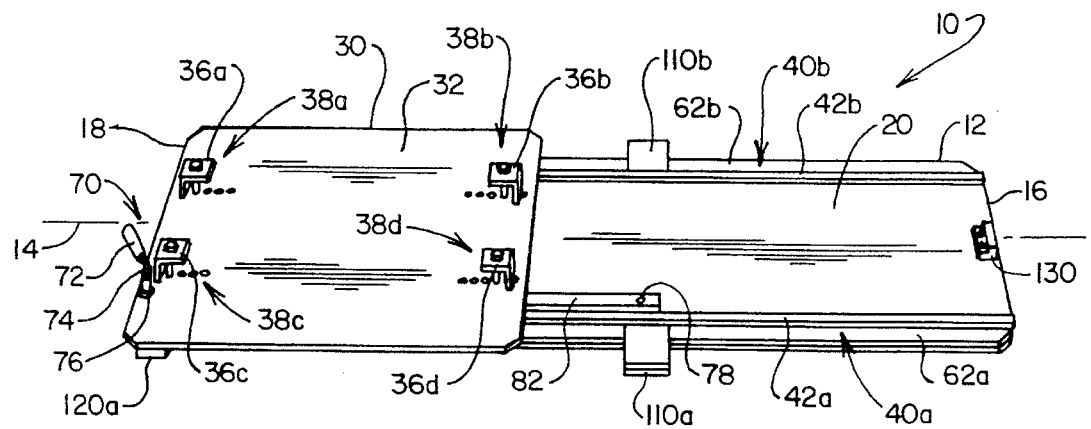
FIG. 3 is a perspective view of the positioning system of FIG. 1 shown in a rearward orientation for disposing the examination chair at its rearward position.

The drawings will be described further in connection with the following Detailed Description of the Invention.

DETAILED DESCRIPTION OF THE INVENTION

Referring initially to FIGS. 1–4, shown generally at 10 is the platform of a positioning system in accordance with the present invention for positioning an ophthalmic examination chair having an associated instrument stand between a forward position spaced a predetermined distance from an eye examination target and a rearward position providing access to the instrument stand by a patient in a wheel chair. Platform 10 may be seen to comprise a lower base, 12, extending along a longitudinal axis, 14, between a forward end, 16, and a rearward end, 18, and to and have an upper surface, 20, and a lower surface 22. It will be appreciated in view of the disclosure to follow hereinafter that base 12 is configured as having a widthwise extent, preferably of about 18 inches (46 cm) which is receivable between the 20 inch (51 cm) to 22 inch (56 cm) wheel spans of most wheel chairs.

Supported on the upper surface 20 of base 12 is an upper carriage, 30, having a top surface, 32, configured to receive the examination chair thereon, and an oppositely-disposed bottom surface, 34. In this regard, top surface 32 of carriage 30 is provided with a number of mounting brackets, 36a–d, for retaining the base of the examination chair. Mounting brackets 36 are made adjustable through their association with the mounting holes shown at 38a–d formed into the top surface 32 of carriage 30. Top surface 32 preferably is provided as having minimum plan dimensions of 24 inches (61 cm) by 25 inches (63.5 cm) to accommodate the bases of most of the examination chairs currently in use.

Figure 4:
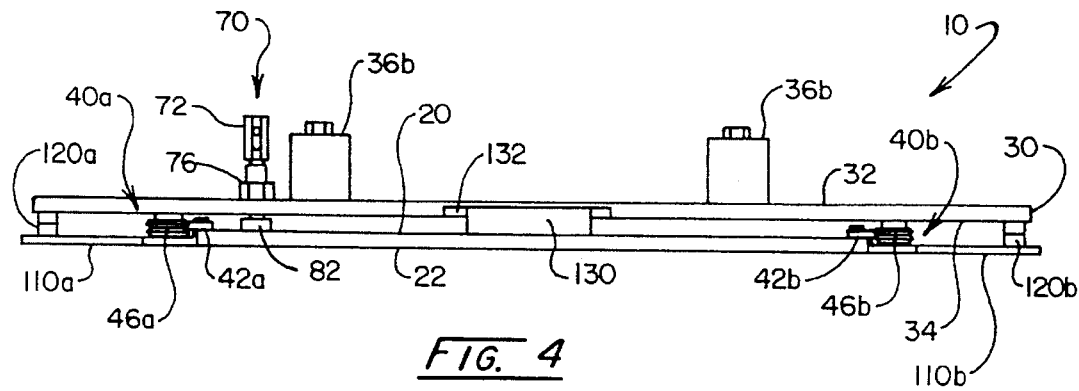
FIG. 4 is a forward end view of the platform of FIG. 3.

Carriage 30 is supported on base 12 for movement between forward and rearward ends 16 and 18 thereof along longitudinal axis 14. Such movement will be appreciated to effect the positioning of the examination chair carried on top surface 32 between the forward position spaced a predetermined distance from an eye examination target, as is shown in FIGS. 1 and 2, and the rearward position providing access to the instrument stand, as is shown in FIGS. 3 and 4. With the lengthwise dimension of base 12 being selected as about 55 inches (140 cm), carriage 30 is provided with a uniaxial travel of about 30 inches (76 cm). Such a travel is sufficient to give wheel chair access to the instrument stand associated with the examination chair, but is not so long as to require the reconfiguration of the typical examination room to provided more room behind the examination chair than is normally available.

For supporting carriage 30 on base 12, a guide assembly, shown generally at 40*a* and 40*b*, may be interposed between the upper surface 20 of base 12 and the bottom surface 34 of carriage 30. Guide assembly 40 will be appreciated to assist in guiding the movement of carriage 30 along longitudinal axis 14 of base 12 between the forward and rearward ends 16 and 18 thereof. In this regard, as may be seen with additional reference to FIG. 5, guide assembly 40 preferably is provided as a pair of spaced-apart guide rails, 42*a* and 42*b*, mounted onto the upper surface 20 of base 12 to extend intermediate the forward and rearward ends 16 and 18 thereof generally parallel to longitudinal axis 14. At least one and, preferably, two sets of guide roller pairs, 44*a–b* and 46*a–b*, are mounted with a corresponding flathead screw or the like, one of which is shown at 47, to the bottom surface 34 of carriage 30. Each of guide rollers 44 and 46 engages a corresponding one of guide rails 42 for the movement of carriage 30 thereon. For minimizing the profile of platform 10, it is preferred that each of guide rollers 44 and 46 are horizontally mounted to carriage 30 to rotate about an axis of rotation, represented at 48, which is generally perpendicular to bottom surface 34. In this way, the overall height of platform 10 may be maintained at from about 1 inch (2.5 cm) to about 1.5 inch (4 cm), thereby minimizing the step from which an ambulatory patient, whose eyes may be dilated or other otherwise unaccommodated, must take to exit the examination chair.

Figure 5:
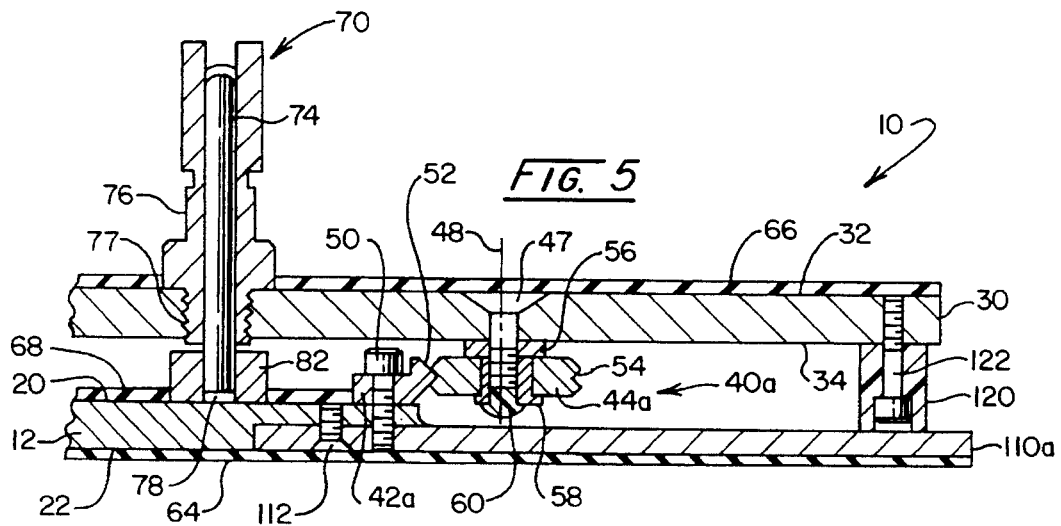
FIG. 5 is a cross-sectional view, shown in enhanced detail, taken through line 5—5 of FIG. 1 and illustrating one embodiment of a locking assembly for releasably locking the examination chair at its forward and its rearward position.

As may be seen best through continuing reference to FIG. 5, each of guide rails 42, which may be secured to the upper surface 20 of base 12 via a number of socket head screws, one of which is shown at 50, are configured as having an apexed, generally V-shaped profile disposed laterally with respect to upper surface 20. As is shown at 52, the apex of each of rails 42 is disposed outwardly with respect to base 12 to be engaged by a corresponding roller 44 or 46. In this regard, the periphery, 54, of each of guide rollers 44 and 46 is configured as having a generally V-shaped notch portion formed thereinto for receiving the corresponding one of guide rails 42. An associated washer, 56, and bushing, 58, are coaxially disposed with each of guide rollers 44 and 46. As is shown, bushing 58 may be eccentrically configured for rotatably adjusting the tension or rolling resistance between rollers 44 and 46 and guide rails 42. Guide rails 42 and guide rollers 44 and 46 of the type herein described are manufactured by the Bishop-Wisecarver Corp. under the name of DUA-L-VEE® Guide Wheel Systems. A cap, 60, preferably formed of a polymeric material such as a nylon having a low frictional coefficient, may be inserted into bushing 58 to provide a bearing surface should carriage 30 be overloaded or should base 12 undergo a flexion or other bending moment. With guide rails 42 and guide rollers 44 and 46 provided as described, and with a standard examination chair mounted to carriage 30, it has been determined that a push force of only from about 10 lb (4.5 kg) to a maximum of about 20 lb (9 kg) is necessary to move the chair from the forward to the rearward position.

As it is anticipated that platform 10 will be used on carpeted surfaces and the like, there is presented the hazard that carpet fibers and the like may work to foul guide rails 42 and guide wheels 44 and 46, thereby restricting the free movement of carriage 30. Accordingly, as is shown at 62*a–b* in FIGS. 1 and 3, rails 42 may be inwardly spaced from the outer periphery of base 12 to form flanged portions protecting the rails from the ingress of fibrous material or the like. Further, as it is anticipated that base 12 may not be fastened to the floor surface, lower surface 22 thereof may be provided, as is shown at 64 in FIG. 5, with a covering having a coefficient of static friction selected as effective to delimit the movement of base 12 as carriage 30 is moved along longitudinal axis 14 thereof. Covering 64 preferably is provided as a anti-skid, ribbed material formed of a polymeric material such as a vinyl or the like which is oriented with its ribs extending generally perpendicular to longitudinal axis 14. As is shown at 66 and 68, covering 64 also may be provided on the upper surface 32 of carriage 30, and on the top surface of 20 of base 12 to prevent slipping should a patient or operator accidentally step thereon. Preferably, the covering 64 provided on the upper surface 32 of carriage 30 and on the top surface of 20 of base 12 again is provided as a ribbed material, but is oriented with its ribs disposed generally parallel to longitudinal axis 14 for easier cleaning.

Continuing with reference to FIG. 5 in conjunction with FIGS. 1–4, a locking assembly is shown at 70 for releasably locking carriage 30 in its forward and rearward orientations. In this way, platform 10 is made to be self-positioning to return the examination chair to its calibrated forward position after being moved to its rearward position providing wheel chair access to the instrument stand. As may be seen in FIG. 5, assembly 70 may be configured as a hand-actuable lever extending to a pin, 74, which, in turn, extends through a housing, 76, which housing is received through a pin aperture, 77, formed into carriage 30. A corresponding forward aperture, 78, and rearward aperture, 80, are provided in base 12 to receive pin 74 thereinto locking carriage 30 in its forward (FIGS. 1 and 2) or rearward (FIGS. 3 and 4) orientation disposing the examination chair in its forward and rearward positions, respectively. As is shown, apertures 78 and 80 may be provided in base 12 as being formed into a separate lock pin block, 82, mounted onto the upper surface 20 base 12. Lock pin block 82, which may be formed of an acetal polymer or the like, additionally may be provided as having a plurality of medial apertures, two of which are shown at 84*a* and 84*b*, configured to receive pin 74 to lock carriage 30 in a predetermined orientation disposing the examination chair at a position intermediate its forward and rearward positions. Lock pin assemblies such as that described in connecting with assembly 70 are manufactured by the Reid Tool Company under the part number SSFR-50. Advantageously, such assemblies are provided to be spring-loaded to downwardly bias pin 74 into a corresponding aperture 78, 80, or 84. In this manner, a measure of safety is attained in that carriage 30 is automatically maintained in a locked orientation.

Figure 5A:
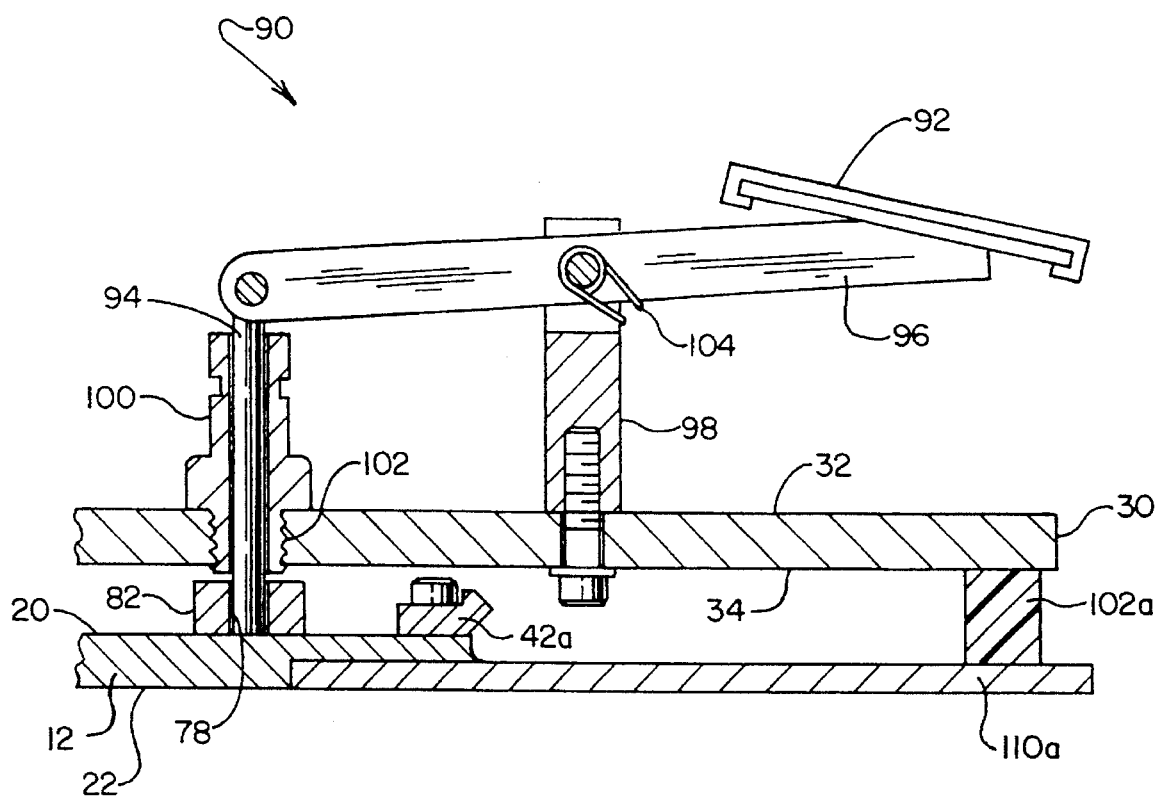
FIG. 5A is a cross-sectional view showing an alternative embodiment of the locking assembly of FIG. 5.

Looking next to FIG. 5A, an alternative assembly for locking carriage 30 in its forward and rearward orientations is shown generally at 90 to comprise a foot-actuable arrangement comprising a pedal, 92, pivotally coupled to a lock pin, 94, via a lever arm, 96, and a pivot support, 98. Pin 94 is received into a housing, 100, which extends through a pin aperture, 102, formed into carriage 30 and into forward or rearward aperture 78 or 80 of block 82. Again, as is shown at 104, assembly 90 may be provided to be spring-loaded to downwardly bias pin 94 into a corresponding aperture 78 or 80.

Returning to FIGS. 1–5, base 12 is shown as having a pair of stabilizer members, 110*a* and 110*b*, extending outwardly from opposite sides thereof intermediate forward end 16 and rearward end 18. As is shown in FIG. 5 for stabilizer member 110a, each of stabilizer members 110 may be attached to base 12 with a mechanical fastener such as the flathead machine screw shown at 112. The outward extension of stabilizer members 110 increases the lateral stability of platform by increasing the moment of force necessary to effect the tilting of base 12 from patient and/or chair imposed movements. Moreover, and as is detailed hereinafter in connection with FIG. 7, with carriage 30 disposed in its rearward orientation, each of members 110 are configured to abuttingly engage a wheel of the wheel chair being moved rearwardly straddling base 12. By virtue of this abutting engagement, the wheel chair thereby is positioned at the forward position spaced the calibrated distance from the eye target. Thus, platform 10 may be seen to be advantageously self-positioning both with respect to the positioning of the examination chair for ambulatory patients and with respect to the positioning of the wheel chairs of disabled patients.

It will be appreciated that in its forward orientation (FIGS. 1 and 2), carriage 30 will be supporting the combined weight of the examination chair plus that of the ambulatory patient being examined. As such combined weight may exceed 500 lbs (225 kg), it is preferred that carriage 30 be further supported when in its forward orientation. Accordingly, a pair of support members or pads, 120a and 120b, are shown mounted with a machine screw or the like, one of which is shown at 122 of FIG. 5, to the bottom surface 34 of carriage 30 on opposite sides thereof. As is shown in FIGS. 2 and 5, with carriage 30 moved into its forward orientation, each of support members 120 are received on and bear upon a respective one of stabilizer members 110. As was pin block 82, it is preferred that support members 120 are formed of a polymeric material such as an acetal polymer or the like having a relatively low coefficient of friction.

For still further supporting carriage 30 when in its forward orientation, a forward stop member, 130, again formed of an acetal polymer or the like, is mounted to the upper surface 20 of base 12 at the forward end 16 thereof. Forward stop member 130 preferably is formed as having a generally L-shaped profile configured to abuttingly receive and support a corresponding forward cavity, 132, formed into the bottom surface 34 of carriage 30. With forward stop member 132 and support members 120 provided as shown, a stable, three-point support of carriage 30 is achieved when disposed in its forward orientation. The abutting engagement effected between carriage 30 and forward stop member 130 also will be seen to delimit the travel of carriage 30 beyond the extent of rails 42, thereby keeping carriage 30 supported on base 12. In this regard, a rearward stop member, 134, additionally may be mounted to the upper surface 20 of base 12 at the rearward end 18 thereof to abutting engage carriage 30 when disposed in its rearward orientation. As was forward stop member 130, rearward stop member 134 preferably is formed of an acetal material and is configured as having a generally L-shaped profile to abuttingly receive and support a corresponding rearward cavity, 136, formed into the bottom surface 34 of carriage 30.

As to the materials of construction for forming platform 10 of the present invention, it is preferred for weight considerations that carriage 30 and base 12 be formed of a material such as a 6061-T6 aluminum or the like having a relatively high strength to weight ratio. For rigidity and wear considerations, however, it is preferred that stabilizer members 110, guide rails 42, and guide wheels 46 be constructed of a stainless, cold rolled, or otherwise hardened steel. As aforementioned, pin block 82, support members 120, and forward and rearward stop members 130 and 134 preferably are constructed of a polymeric material, such as an acetal or the like, having a relatively low coefficient of friction. So constructed, platform 10 has been found to have a weight of about 73 lbs (33 kg).

Laboratory testing of the position system described in connection with platform 10 has involved cyclic testing of carriage 30 as well as stability testing. For the cyclic testing, platform 10 was positioned on a carpeted surface, and a commercially-available examination chair (R.H. Burton Company, Grove City, Ohio) was mounted onto carriage 30 thereof. An additional weight of 244 lbs (111 kg) was placed in the chair to give a total weight of 486 lbs (220 kg) supported by the platform 10. Carriage 30 then was operated for 3200 cycles, with each cycle consisting of a stroke from either the forward end 16 or the rearward end 18 of base 12 to the opposite end, an impact with the corresponding stop member 130 or 134, and a return stroke and impact with the other stop member 130 or 134. The impact velocity of the carriage 30 with the stop members 130 and 134 was maintained at 1000 in/min (2540 cm/min). A visual inspection following the completion of the 3200 test cycles revealed no mechanical or structural failures in either the carriage 30 or the stop members 130 and 134. Further, only limited wear was noted.

The stability testing of platform 10 involved both front and rear tip testing as well as side stability testing. For the rear tip testing, with the examination chair mounted onto carriage 30 and the seat back thereof positioned in a horizontal or reclined position, a weight of 173 lbs (78 kg) was placed in the chair just rearward of the pivot of the seat back. A calibrated force gauge then was used to applied a normal force to the seat back just rearward of the weight. The force required to lift the forward edge of base 12 was recorded at 97 lbs (44 kg), which well exceeded the 35 lbs (16 kg) required under BIFMA X5.1, §13.

For the front tip testing, the examination chair was mounted onto carriage 30 with no added weight. With the seat back of the chair disposed in an upright position, a calibrated force gauge was used to apply a forward and downward force at a 45° angle with respect to the chair. The force required to lift the rear edge of the chair was recorded at 170 lbs (77 kg), which well exceeded the 97 lbs (44 kg) required under BIFMA X5.1, §13.

For the side stability testing, the examination chair was mounted onto carriage 30 with the seat back thereof disposed in an upright position and with 173 lbs (78 kg) placed on the seat. A calibrated force gauge was used to apply a horizontal force normal to one arm of the chair. The force required to lift the opposite edge of base 12 was recorded as 120 lbs (54 kg), which well exceeded the BIFMA criteria for both the front and rear stability tests.

Figure 6:
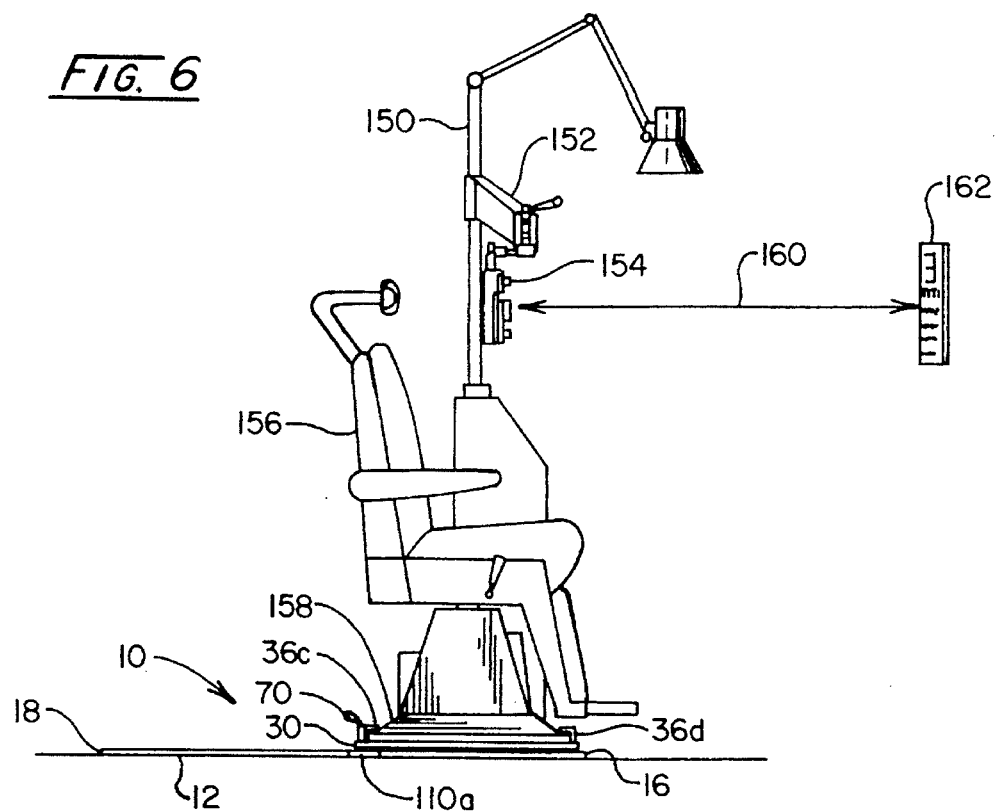
FIG. 6 is a schematic view illustrating the method of the present invention wherein an ophthalmic examination chair having an associated instrument stand is shown mounted to the positioning system of FIG. 1 and disposed at a forward position spaced a predetermined distance from an eye examination target.
Figure 7:
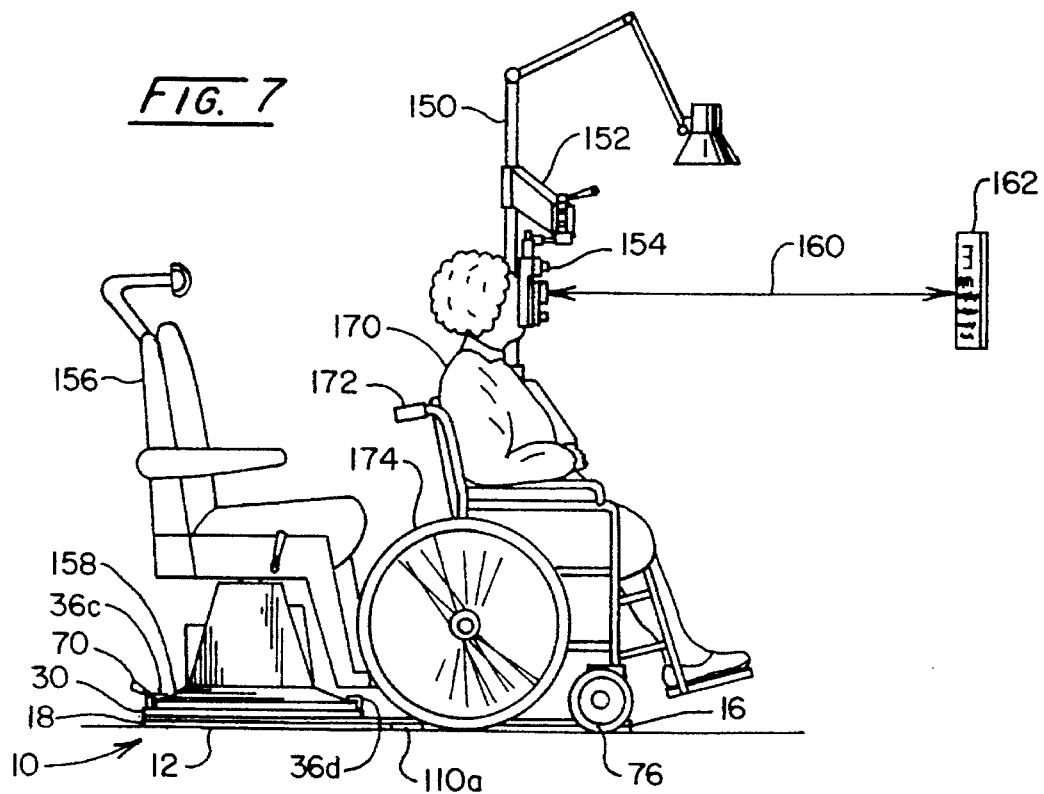
FIG. 7 is a schematic view further illustrating the method of the present invention wherein the examination chair of FIG. 6 is shown disposed at a rearward position providing access to the instrument stand by a patient in a wheel chair.

Referring now to FIGS. 6 and 7, next considered are the steps involved in the method of the present invention for providing access by a patient in a wheel chair to an ophthalmic instrument stand having an associated examination chair. Looking initially to FIG. 6, an instrument stand is shown at 150 as having an movable arm, 152, extending therefrom on which is mounted an ophthalmic refractor, 154, configured to be placed confronting the eyes of the patient being examined. Although it is illustrated as having only arm 153 and refractor 154, it will be appreciated that stand 150 may be provided as supporting other instruments such as a keratometer and a slit lamp, as well as a holder for such hand-held diagnostic instruments as an ophthalmoscope and a retinoscope. Indeed, the facile provision of wheel chair access to all of the eye examination instruments needed for a complete eye examination is specifically seen as a precept of the present invention. Instrument stand 150 further is shown with an associated examination chair, 156, having a base, 158, mounted with clamps 36 to carriage 30 of platform 10. As is illustrated, carriage 30 is locked with assembly 70 in a forward orientation locking examination chair 156 in a forward position spaced a predetermined distance, represented at 160, from an eye examination target such as an eye chart, 162, or the like. In such position, examination chair 156 may receive an ambulatory patient or the like for examination.

Looking next to FIG. 7, carriage 30 is shown as having been translated rearwardly along base 12 from the forward end 16 to the rearward end 18 thereof into a rearward orientation disposing examination chair 156 in a rearward position providing access to instrument stand 150 by a disabled patient, 170, confined to a wheel chair, 172, having wheels 174 and 176. Wheel chair 172 is shown as having been moved rearwardly over the base 12 of platform 10 with the widthwise extent thereof being received between the span of wheels 174 and 176. For non-standard chairs such as custom or children's chairs, however, it will be appreciated that one or both wheels thereof may be rolled onto base portion 12 should the widthwise extent thereof not be receivable between the wheel span. Once moved rearwardly over base 12, wheel chair 172 may be positioned at the forward position spacing patient 170 a predetermined distance 160 from eye chart 162. In this regard, it may be seen that an abutting engagement may be effect between wheels 174 of wheel chair 172 and stabilizer members 110 extending outwardly from base 12, which engagement delimits the rearward movement of wheel chair 172 and thereby locates the chair at the forward position.

Thus, a method is described which provides efficient wheel chair access to instrument stand 150 in a minimum amount of space and time, and which allows the disabled patient 170 to remain seated in her wheel chair. It will be appreciated that, by virtue of the present invention, examination chair 156 may be moved and disable patient 170 may be properly positioned with considerable speed. As most providers examine patients only according to a predetermined exam schedule which affords each patient only a certain amount of exam time, and as the provider may not be informed beforehand as to the disability of the particular patient to be examined next according to the schedule, the ability to quickly accommodate for that disability will be seen to be especially desirable.

It is anticipated that certain changes may be made in the present invention without departing from the precepts herein involved. For example, although the present invention has been illustrated in connection with the retrofitting of an existing examination chair, it will be appreciated that the advantages of the invention are such that it may be integrally incorporated into the chair as part of the base thereof. Accordingly, it is intended that all matter contained in the foregoing description shall be interpreted as illustrative and not in a limiting sense.

What is claimed:

1. A positioning system for providing access by a patient in a wheel chair to an ophthalmic instrument stand having an associated examination chair normally disposed at a forward position spaced a predetermined distance from an eye examination target comprising:

a lower base portion extending a length of about 55 inches along a longitudinal axis between a forward end and a rearward end, said base portion having an upper and a lower surface;

an upper carriage portion supported on the upper surface of said base portion having a bottom surface and a top surface, configured to receive said examination chair thereon, said carriage normally being supported on the upper surface of said base portion at said forward position a guide assembly interposed between the bottom surface of said carriage portion and the upper surface of said base potion, said guide assembly providing said support of said carriage portion on said base portion and guiding the movement of said carriage portion along said longitudinal axis of said base portion into and a predetermined distance away from said forward position, said predetermined distance being selected to provide access for said wheelchair at said forward position; and a locking assembly for releasably locking said carriage portion in a forward orientation disposing said examination chair at said forward position, and in a rearward orientation disposing said examination chair at said rearward position.

2. The positioning system of claim 1 in which said predetermined distance is about thirty inches.

3. The positioning system of claim 1 further comprising a forward stop member mounted to the upper surface of said base portion at the forward end thereof, said stop member configured to abuttingly engage said carriage portion when disposed in said forward position.

4. The positioning system of claim 3 further comprising a rearward stop member mounted to the upper surface of said base portion at the rearward end thereof, said stop member configured to abuttingly engage said carriage portion when disposed in said rearward position.

5. The positioning system of claim 1 wherein said guide assembly comprises:

a pair of spaced-apart guide rails mounted on the upper surface of said base portion to extend intermediate the forward and the rearward end thereof generally parallel to said longitudinal axis; and at least a pair of guide rollers mounted to the bottom surface of said carriage portion to each engage a corresponding one of said guide rails for the movement of said carriage portion thereon along said longitudinal axis.

6. The positioning system of claim 5 wherein:

each of said guide rails is configured as having an apexed, generally V-shaped profile disposed laterally with respect to the upper surface of said base portion, the apex of said profile being disposed outwardly with respect to said base portion; and each of said guide rollers is horizontally mounted to the bottom surface of said carriage portion as having an axis of rotation generally perpendicular thereto, the outer periphery of each of said guide rollers being configured as having a generally V-shaped notch portion formed therein for receiving said corresponding one of said guide rails.

7. The positioning system of claim 1 wherein said locking assembly comprises a pin mounted on said carriage portion, said carriage portion being formed as having a pin aperture configured to receive a portion of said pin therethrough, and said base portion being formed as having a forward aperture configured to receive said pin from said carriage portion to lock said carriage portion in said forward orientation disposing said examination chair at said forward position, and a rearward aperture configured to receive said pin from said carriage portion to lock said carriage portion in said rearward orientation disposing said examination chair at said rearward position.

8. The positioning system of claim 7 wherein said base portion further is formed as having a plurality of medial apertures disposed intermediate said forward and said rearward aperture, each of said medial apertures configured to receive said pin from said carriage portion to lock said carriage portion in a predetermined orientation disposing said examination chair at a position intermediate said forward and said rearward position.

9. The positioning system of claim 4 wherein the lower surface of said base portion is provided with a covering having a coefficient of static friction selected as effective to delimit the movement of said base portion as a consequence of said carriage portion being moved along the longitudinal axis thereof between said forward stop and said rearward stop.

10. The positioning system of claim 9 wherein said covering is formed of a polymeric material having a plurality of ribs oriented to extend generally perpendicular to the longitudinal axis of said base portion.

11. A method of providing access by a patient in a wheel chair to an ophthalmic instrument stand having an associated examination chair disposed at a forward position spaced a predetermined distance from an eye examination target, said method comprising the steps of:

(a) mounting said examination chair on a platform comprising:
  a lower base extending along a longitudinal axis between a forward end and a rearward end, said base having an upper and a lower surface and a widthwise extent configured as being receivable between the wheels of said wheel chair; and
  an upper carriage having a bottom surface and a top surface configured to receive said examination chair thereon, said carriage being supported on the upper surface of said base for movement between the forward and the rearward end thereof along said longitudinal axis to position said examination chair at said forward position and at a rearward position providing access to said instrument stand by said patient in said wheel chair;

(b) moving said carriage of said platform rearwardly along the longitudinal axis of said base to move said examination chair from said forward position to said rearward position;

(c) moving said wheel chair rearwardly over said base of said platform, the widthwise extent of said base being received between the wheels of said wheel chair; and (d) positioning said wheel chair at said forward position to space said patient at said predetermined distance from said eye target.

12. The method of claim 11 wherein said platform is provided as further comprising at least one stabilizer member extending outwardly from said base intermediate the forward and the rearward end thereof, said stabilizer member being configured to abuttingly engage a wheel of said wheel chair delimiting the rearward movement thereof for positioning said wheel chair at said forward position.

13. The method of claim 11 wherein said platform is provided as further comprising a pair of oppositely-disposed stabilizer members extending outwardly from opposite sides of said base intermediate the forward and the rearward end thereof, each of said stabilizer members being configured to abuttingly engage a wheel of said wheel chair delimiting the rearward movement thereof for positioning said wheel chair at said forward position.

14. The method of claim 13 wherein said platform is provided as further comprising a pair of support members mounted to the bottom surface of said carriage on opposite sides thereof, each of said support members being received on a respective one of said stabilizer members for supporting said carriage when disposed in said forward position.

15. The method of claim 14 wherein said platform is provided as further comprising a forward stop member mounted to the upper surface of said base at the forward end thereof, said stop member being configured to abuttingly support said carriage when disposed in said forward position.

16. The method of claim 11 wherein said platform is provided as further comprising a forward stop member mounted to the upper surface of said base at the forward end thereof, said stop member configured to abuttingly engage said carriage when disposed in said forward position.

17. The method of claim 16 wherein said platform is provided as further comprising a rearward stop member mounted to the upper surface of said base at the rearward end thereof, said stop member configured to abuttingly engage said carriage when disposed in said rearward position.

18. The method of claim 11 wherein the lower surface of said base of said platform is provided with a covering having a coefficient of static friction selected as effective to delimit the movement of said base as said carriage is moved along the longitudinal axis thereof.

19. The method of claim 18 wherein said covering is provided as a polymeric material having a plurality of ribs oriented to extend generally perpendicular to the longitudinal axis of said base portion.

20. A positioning system for moving an ophthalmic examination chair used in conjunction with an associated instrument stand from a forward position spaced a predetermined distance from an eye examination target comprising:

a lower base portion extending along a longitudinal axis between a forward end and a rearward end, said base portion having an upper widthwise extent configured as being receivable between the wheels of a wheel chair;

an upper carriage portion having a bottom surface and a top surface configured to receive an examination chair thereon, said carriage being supported on the upper surface of said base portion for movement between the forward and the rearward end thereof along said longitudinal axis to position said examination chair at said forward position and at a rearward position for providing access to the instrument stand by a patient in said wheel chair, at least one stabilizer member extending outwardly from said base portion intermediate the forward and the rearward end thereof for stabilizing said base portion, said stabilizer member being configured to abuttingly engage a wheel of said chair for positioning said wheel chair at said forward position; and a locking assembly for releasably locking said carriage portion in a forward orientation disposing said examination chair at said forward position, and in a rearward orientation disposing said examination chair at said rearward position.

21. A positioning system for moving an ophthalmic examination chair used in conjunction with an associated instrument stand from a forward position spaced a predetermined distance from an eye examination target comprising:

a lower base portion extending along a longitudinal axis between a forward end and a rearward end, said base portion having an upper and a lower surface and a widthwise extent configured as being receivable between the wheels of a wheel chair;

an upper carriage portion having a bottom surface and a top surface configured to receive said examination chair thereon, said carriage being supported on the upper surface of said base portion for movement between the forward and the rearward end thereof along said longitudinal axis to position said examination chair at said forward position and at a rearward position for providing the instrument stand by a patient in said wheel chair;

a pair of oppositely-disposed stabilizer members extending outwardly from opposite sides of said base portion intermediate the forward and the rearward end thereof for stabilizing said base portion, each of said stabilizer members being configured to abuttingly engage a wheel of said wheel chair for positioning said wheel chair at said forward position; and a locking assembly for releasably locking said carriage portion in a forward orientation disposing said examination chair at said forward position, and in a rearward orientation disposing said examination chair at said rearward position.

22. The positioning system of claim 21 further comprising a pair of support members mounted to the bottom surface of said carriage portion on opposite sides thereof, each of said support members being received on a respective one of said stabilizer members for supporting said carriage when disposed in said forward position.

23. The positioning system of claim 22 further comprising a forward stop member mounted to the upper surface of said base portion at the forward end thereof, said stop member being configured to abuttingly support said carriage portion when disposed in said forward position.

24. A method of providing access by a patient in a wheel chair to an ophthalmic instrument stand having an associated examination chair disposed at a forward position spaced a predetermined distance from an eye examination target, said method comprising the steps of:

(a) mounting said examination chair on a platform comprising:

a lower base portion extending a length of about 55 inches along a longitudinal axis between a forward end and a rearward end, said base portion having an upper and a lower surface;

an upper carriage portion supported on the upper surface of said base portion having a bottom surface and a top surface, configured to receive said examination chair thereon, said carriage normally being supported on the upper surface of said base portion at said forward position;

a guide assembly interposed between the bottom surface of said carriage portion and the upper surface of said base portion, said guide assembly providing said support of said carriage portion on said base portion and guiding the movement of said carriage portion along said longitudinal axis of said base portion into and a predetermined distance away from said forward position, said predetermined distance being selected to provide access for said wheelchair at said forward position; and (b) moving said carriage of said platform rearwardly along the longitudinal axis of said base to move said examination chair from said forward position to said rearward position;

(c) moving said wheel chair rearwardly over said base of said platform; and (d) positioning said wheel chair at said forward position to space said patient at said predetermined distance from said eye target.

25. The method of claim 24 wherein said platform is provided as further comprising a forward stop member mounted to the upper surface of said base at the forward end thereof, said stop member configured to abuttingly engage said carriage when disposed in said forward position.

26. The method of claim 25 wherein said platform is provided as further comprising a rearward stop member mounted to the upper surface of said base at the rearward end thereof, said stop member configured to abuttingly engage said carriage when disposed in said rearward position.

27. The method of claim 25 wherein the lower surface of said base platform is provided with a covering having a coefficient of static friction selected as effective to delimit the movement of said base as said carriage is moved along the longitudinal axis thereof.

28. The method of claim 27 wherein said covering is provided as a polymeric material having a plurality of ribs oriented to extend generally perpendicular to the longitudinal axis of said base portion.

\* \* \* \* \*